United States Patent [19]

Smith et al.

[11] Patent Number: 5,360,573
[45] Date of Patent: Nov. 1, 1994

[54] BLEACH PRECURSORS

[75] Inventors: Richard G. Smith, Wirral; David W. Thornthwaite, Neston, both of England

[73] Assignee: Lever Brothers Company, Division of Conopco, Inc., New York, N.Y.

[21] Appl. No.: 926,074

[22] Filed: Aug. 5, 1992

[30] Foreign Application Priority Data

Aug. 6, 1991 [GB] United Kingdom ............ 9116939.1

[51] Int. Cl.$^5$ ................................................. C09K 3/00
[52] U.S. Cl. .......................... 252/186.39; 252/186.38
[58] Field of Search ..................... 252/186.38, 186.39

[56] References Cited

U.S. PATENT DOCUMENTS

| | | | |
|---|---|---|---|
| 2,955,905 | 10/1960 | Davies et al. | 8/111 |
| 3,901,819 | 8/1975 | Nakagawa et al. | 252/186.38 |
| 4,800,038 | 1/1989 | Broze et al. | 252/174.17 |
| 5,273,674 | 12/1993 | Kottwitz et al. | 252/95 |

FOREIGN PATENT DOCUMENTS

| | | |
|---|---|---|
| 0380437 | 8/1990 | European Pat. Off. |
| 89/01480 | 2/1989 | WIPO |
| 9110719 | 7/1991 | WIPO |

OTHER PUBLICATIONS

Tetrahedron Letters, vol. 28, No. 33, pp. 3809–3812, 1987.
Tetrahedron Letters, vol. 42, No. 9, pp. 2457–2467, 1986.
"Enzymes in Carbohydrate Synthesis: Lipase-Catalyzed Selective Acylation and Deacylation of Furanose and Pyranose Derivatives", Hennen, et al, *J. Org. Chem.*, 1988, No. 53, pp. 4939–4945.
"Lehrbuch der Organischen Chemie", Carl R. Noller, 1960, pp. 396–397.
Synthesis of Glycosyl Trifluoroacetates and Their Reactions with Carboxylic M. Kobayashi et al; Chem. Pharm. Bull., 1986, No. 10, p. 4069.
Chemoselective Deprotection of 1-O-Acyl Sugar Derivatives, G. Grynkiewicz J. Chem. Research (S), 1989, pp. 152–153.
CA117(3):26993K "Radical-Mediated Halogenations of Anomerically N–Substituted Glucopyranosyl Derivatives", Praly et al., Univ. Lyon France, 1992.
CA113(17):152912P "Synthesis of Trehalose Homolog, 6-Deoxy-.α. -D-Gluco-Heptopyranosyl etc."; Breton et al., Univ. Ottawa Canada, 1990.
CA112(19):179703n "Azidochlorination and Diazidization of Glycals", Naicker et al. (Biomira Inc., Can.).

*Primary Examiner*—Robert L. Stoll
*Assistant Examiner*—Joseph D. Anthony
*Attorney, Agent, or Firm*—Milton L. Honig

[57] ABSTRACT

Bleaching compositions comprising peroxy acid bleach precursors preferably based on acetylated pentose, hexose or lactose.

7 Claims, No Drawings

BLEACH PRECURSORS

This invention relates to novel peroxyacid bleach precursors, and their use in bleaching and bleach detergent compositions.

Detergent bleach compositions for washing at high temperatures, that is temperatures greater than 60° C., are well known in the art. Such compositions generally contain, as bleaching agent, a peroxide compound which liberates hydrogen peroxide in aqueous solution, such as peroxyhydrates, including alkali metal perborates, percarbonates, perphosphates, persulphates and persilicates, urea peroxide and the like. These bleaching agents are only effective at higher temperatures of at least 80° C.

It is known the bleach activity of peroxide bleach compounds may be improved so that they become effective at lower wash temperatures, for example 40°-60° C., by the use of peroxyacid bleach precursors, often also referred to as bleach activators.

Numerous substances have been disclosed in the art as bleach activators.

British Patents 836,988 and 864,798 (UNILEVER) are examples of earlier patents in the field relating to this technology. They disclose several classes of esters, including the benzoyl ester of sodium phenol sulphonate (SBOBS) and sodium-p-acetoxybenzene sulphonate (SABS).

Another early patent in this field is British Patent 855,735 which discloses the broad class of "acyl organoamides", to which the currently most widely used peracetic acid, precursor N,N,N′,N′-tetraacetyl ethylene diamine (TAED), belongs.

A series of articles by Allan H. Gilbert in Detergent Age, June 1967, pages 18-20; July 1967, pages 30-33 and August 1967, pages 26, 27 and 67, disclose a further collection of various bleach activator compounds.

Indeed the majority of bleach-containing fabric washing products currently on the market use a TAED/perborate bleach system. This combination is capable of generating peracetic-acid in the wash, thus achieving useful bleaching effects at temperatures lower than those necessary for sodium perborate (=hydrogen peroxide) bleaching. At still lower wash temperatures, e.g. 40° C. and below, however, the rate of perhydrolysis of TAED (the bleach precursor) and consequently the bleaching performance are much reduced. These problems may be overcome by the use of 1) faster acting bleach precursors, and/or 2) precursors that yield more reactive peroxyacids, more hydrophobic peroxyacids, or cationic peroxyacids. Representative of the first class of precursors is, for example, sodium p-acetoxy benzene sulphonate (SABS) as disclosed in British Patent No's 836,988 and 864,798; representatives of the second class of precursors, are for example, sodium-p-benzoyloxy benzene sulphonate which yields the more reactive peroxybenzoic acid and is disclosed in GB Patent no. 836,988; sodium-p-nonanoyloxybenzene sulphonate and sodium p-3,5,5,-trimethylhexanoyloxy benzene sulphonate as disclosed in EP-A-0098.129 and EP-A-0 120.591 respectively, which yield the more hydrophobic peroxynonanoic and peroxyisononanoic acids; 2-(N,N,N-trimethylammonium) ethyl-4-sulphophenyl carbonate (SPCC) disclosed in U.S. Pat. No. 4,751,015 which yields, the cationic peroxyacid $(CH_3)_3N^+—CH_2—CH_2—OCO_3H$, and the cationic peroxyacid precursors disclosed in EP-A-0 331,229 which yield quaternary ammonium substituted peroxybenzoic acids.

A common characteristic common to all of these faster reacting and more effective peroxyacid precursors is that they have in their structure a leaving group derived from phenol sulphonate i.e.—O—$C_6H_4$—$SO_3Na$, which is a petrochemical product and expensive to synthesis.

EP-A-0 380 437 discloses $C_6$-$C_{20}$ fatty acyl monoesters of hexose or pentoses. These compounds whilst having satisfactory surfactant properties are not as effective bleach precursors as would be expected.

Another class of bleach activator recently proposed (WO91/10719) are those based on pentose or hextose having a long-chain acyl group preferably having at least eight carbon atoms.

It is an object of the present invention to provide an peroxyacid bleach precursor which is effective at lower wash temperatures over a wide class of stains.

Another object of the invention is to provide an effective bleaching and/or detergent composition comprising peroxyacid bleach precursor; the composition having improved overall bleaching capacity at lower wash temperatures.

These and other objects of the present invention will become more readily apparent from the further detailed description and examples.

It has now been found that the above objects can be achieved if the peroxyacid bleach precursor is a sugar derivative selected from the group of compounds having the following general formula:

$$R^I—CH(CHOAc)_n(CR^{II}OCOR)O \quad (I)$$

$$OCH(CH_2OAc)(CHOAc)_3CH—O—CH(CHOAc)_2(CHOCOR^{IV})OCH(CH_2OAc) \quad (II)$$

wherein $$CH_3\overset{O}{\underset{\|}{C}}—;$$

$R^I$ and $R^{II}$ may each independantly be $AcOCH_2$ or H; and

R is selected from the group consisting of
 i) linear or branched chain $C_3$-$C_6$ alkyl, alkenyl or alkynyl groups,
 ii) phenyl and substituted phenyl,
 iii) $C_1$-$C_4$ alkyl phenyl, $CH_2OCOR^{III}$ and $CH_2NHCOR^{III}$ wherein $R^{III}$ is R; and
 iv) quaternary ammonium substituted derivatives of ii), iii) and $C_{3-19}$ alkyl, alkenyl or alkynyl groups; and n is 2 or 3.

$R^{IV}$ is selected from the group consisting of
 v) linear or branched chain $C_{3-19}$ alkyl, alkenyl or alkynyl groups;
 vi) phenyl and substituted phenyl;

vii) $C_{1-4}$ alkyl phenyl, $CH_2OCOR^V$ and $CH_2NHCOR^V$ wherein $R^V$ is $R^{IV}$; and viii) quaternary ammonium substituted derivatives of groups v), vi), vii).

Accordingly the invention provides a bleaching composition comprising (a) a peroxyacid bleach precursor having a formula selected from:

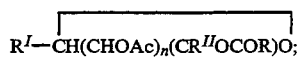  (I)

$R^I$—CH(CHOAc)$_n$(CR$^{II}$OCOR)O;

and

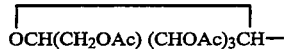  (II)

OCH(CH$_2$OAc) (CHOAc)$_3$CH—

—O—CH(CHOAc)$_2$(CHOCOR$^{IV}$)OCH(CH$_2$OAc)

wherein:

CH$_3$C—;

$R^I$ and $R^{II}$ may each independantly be $AcOCH_2$ or H; and

R is selected from the group consisting of i) linear or branched chain $C_3$-$C_6$ alkyl, alkenyl or alkynyl groups, ii) phenyl and substituted phenyl, iii) $C_1$-$C_4$ alkyl phenyl, $CH_2OCOR^{III}$ and $CH_2NHCOR^{III}$ wherein $R^{III}$ is R; and iv) quaternary ammonium substituted derivatives of ii), iii) and $C_{3-19}$ alkyl, alkenyl or alkynyl groups; and n is 2 or 3.

$R^{IV}$ is selected from the group consisting of v) linear or branched chain $C_{3-19}$ alkyl, alkenyl or alkynyl groups;

vi) phenyl and substituted phenyl;

vii) $C_{1-4}$ alkyl phenyl, $CH_2OCOR^V$ and $CH_2NHCOR^V$ wherein $R^V$ is $R^{IV}$; and viii) quaternary ammonium substituted derivatives of groups v), vi), vii);

and (b) a source of hydrogen peroxide.

Particularly compounds are those of formula (I) wherein n is 3;

$R^I$ is $AcOCH_2$; and $R^{II}$ is H i.e. compounds of formula:

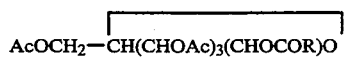

AcOCH$_2$—CH(CHOAc)$_3$(CHOCOR)O

Typical examples of particularly preferred R groups are (I) R=$C_3H_7$ (II) R=$C_5H_{11}$ (III) R=$C_6H_5$ (IV) R=$(CH_3)_3N^+$—$CH_2$—$C_6H_4$ (V) R=$(CH_3)_3N^+$—$(CH_2)_n$, wherein n=1,3 or 5.

The precursors of the invention can be prepared by selectively hydrolysing the most reactive acyl-group of 1,2,3,4,6-pentaacetyl glucose (PAG), or 1,2,3,4-tetraacetylxylose (TAX), or 1,2,3,6-2',3',4',6'-octaacetyllactose (OAL) to produce 2,3,4,6-tetraacetylglucose, or 2,3,4-triacetylxylose, or 2,3,6-2',3',4',6'-heptaacetyllactose respectively, which may then be reacted with an acid chloride or anhydride of choice. In the same way other sugar deratives, such as 1,2,3,4,6-pentaacetylgalactose, 1,2,3,4-tetraacetyllyxose, 1,2,3,4-tetraacetylarabinose, and 1,2,3,6-2',3',4',6'-octa acetylmaltose, after hydrolysis of the most reactive anomeric acetyl group, will produce 2,3,4,6-tetraacetylglactose, 2,3,4-triacetyllyxose, 2,3,4-triacetylarabinose, and 2,3,6-2',3',4',6'-hepta acetylmaltose respectively, which can then be reacted with an acid chloride or anhydride of choice. Other examples of suitable precursors are those derived from acetylated cellibiose, mannose, fructose, melibiose and ribose.

Under normal wash conditions, PAG, TAX or OAL can produce 2–5 moles of peracetic acid. Consequently, the novel precursors of the invention will have the potential to yield both peracetic-acid and another more hydrophobic or more reactive peroxyacid from the same compound e.g.

(i) peroxybutanoic acid (ii) peroxyhexanoic acid (iii) peroxybenzoic acid (iv) trimethylammonium methylene peroxybenzoic acid (v) trimethylammonium peroxyacetic-, peroxybutanoic- or peroxyhexanoic acid.

A key factor enabling the synthesis of these sugar-based precursors is thus the discovery of a method of selectively removing the most reactive acetoxy group (the 1-acetoxy or anomeric acetoxy group) from, for example, pentaacetylglucose, tetraacetylxylose and octaacetyllactose. One synthetic method for preparing the preferred glucose esters involves treating 1,2,3,4,6-pentaacetylglucose (PAG) with 2-aminoethanol in ethylacetate, to produce 2,3,4,6,-tetraacetylglucose, which can then be treated with an acid chloride, e.g. hexanoylchloride, or an anhydride, for example, benzoic anhydride, to yield the fully substituted glucose ester.

Hydrogen peroxide sources are well known in the art. They include the alkali metal peroxides, organic peroxide bleaching compounds, such as the alkali metal perborate, percarbonates, perphosphates, persilicates and persulphates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous bleaching solutions. Sodium percarbonate may be preferred for environmental reasons.

Typically, the molar ratio of hydrogen peroxide (or a peroxide compound generating the equivalent amount of $H_2O_2$) to precursor will range from 0.5:1 to about 20:1, preferably 1:1 to 5:1.

A detergent composition containing a bleach system consisting of an active oxygen-releasing material and peroxyacid bleach precursor will usually also contain surface-active materials, detergency builders and other known ingredients of such formulations.

In such formulations the peroxyacid bleach precursor may be present at a level ranging from about 0.1% to 20% by weight, preferably from 0.5% to 10% by weight, particularly from 1% to 7.5% by weight, together with a peroxide bleaching compound, e.g. sodium perborate mono- or tetra-hydrate, the amount of which is usually within the range of from about 2% to 40%, preferably from about 4% to 30%, particularly from about 10% to 25% by weight.

The surface-active material may be naturally derived, such as soap, or a synthetic material selected from anionic, nonionic, amphoteric, zwitterionic, cationic actives and mixtures thereof. Many suitable actives are commercially available and are fully described in literature, for example in "Surface Active Agents and Detergents", Volumes I and II, by Schwartz, Perry and Berch. The total level of the surface-active material may range up to 50% by weight, preferably being from about 1% to 40% by weight of the composition, most preferably 4 to 25%.

Synthetic anionic surface-actives are usually water-soluble alkali metal salts of organic sulphates and sulphonates having alkyl radicals containing from about 8 to about 22 carbon atoms, the term alkyl being used to include the alkyl portion of higher aryl radicals.

Examples of suitable synthetic anionic detergent compounds are sodium and ammonium alkyl sulphates, especially those obtained by sulphating higher ($C_8$–$C_{18}$) alcohols produced, for example, from tallow or coconut oil; sodium and ammonium alkyl ($C_9$–$C_{20}$) benzene sulphonates, particularly sodium linear secondary alkyl ($C_{10}$–$C_{15}$) benzene sulphonates; sodium alkyl glyceryl ether sulphates, especially those esters of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol alkylene oxide, particularly ethylene oxide, reaction products; the sulphonation products of alkyl esters of fatty acids, particularly the methyl esters; the reaction products of fatty acids such as coconut fatty acids esterified with isethionic acid and neutralized with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $C_{12}$ and then hydrolyzing with a base to produce a random sulphonate; sodium and ammonium $C_7$–$C_{12}$ dialkyl sulfosuccinates; and olefin sulphonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with an anionic surface-active compounds include, in particular, the reaction products of alkylene oxides, usually ethylene oxide, with alkyl ($C_6$–$C_{22}$) phenols, generally 5–25 EO, i.e. 5–25 units of ethylene oxides per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglucosides, e.g. 1-O-alkyl-6-O-acylglucosides, particularly the ethyl glucoside, as disclosed in EP-A-423968; long chain tertiary amine oxides, long chain tertiary phosphine oxides and dialkyl sulphoxides.

Amounts of amphoteric or zwitterionic surface-active compounds may also be present in the compositions of the invention, but this is not normally desired owing to their relatively high cost. If amphoteric or zwitterionic detergent compounds are used, they are generally present in small amounts in compositions based on the much more commonly used synthetic anionic and nonionic actives.

As stated above, soaps may also be incorporated in the compositions of the invention, preferably at a level of less than 25% by weight. They are particularly useful at low levels in binary (soap/anionic) or ternary mixtures together with nonionic or mixed synthetic anionic and nonionic compounds. Soaps which may be used are preferably the sodium, or, less desirably, potassium salts of saturated or unsaturated $C_{10}$–$C_{24}$ fatty acids or mixtures thereof. The amount of such soaps can be varied between about 0.5% and about 25% by weight, with lower amounts of about 0.5% to about 5% being generally sufficient for lather control. Amounts of soap between about 2% and about 20%, especially between about 5% and about 10%, are used to give a beneficial effect on detergency. This is particularly valuable in compositions used in hard water, when the soap acts as a supplementary builder.

The detergent compositions of the invention will generally also contain a detergency builder. Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; dipicolinic acid, nitrilotriacetic acid and its water-soluble salts; alkali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. Nos. 4,144,226 and 4,146,495. Examples of precipitating builder materials include sodium orthophosphate, sodium carbonate and long chain fatty acid soaps. An especially preferred builder system of this class is a mixture of sodium carbonate and calcite.

Examples of calcium ion-exchange builder materials include the various types of water-insoluble crystalline or amorphous aluminosilicates, of which zeolites are the best known representatives.

In particular, the compositions of the invention may contain any one of the known organic or inorganic builder materials, such as sodium or potassium tripolyphosphate, sodium or potassium pyrophosphate, sodium or potassium orthophosphate, calcite sodium carbonate, dipicolinic acid, oxydisuccinic acid; the sodium salt of nitrilotriacetic acid, sodium citrate, carboxymethyloxy malonate, carboxymethyloxy succinate and the water-insoluble crystalline or amorphous aluminosilicate builder materials, or mixtures thereof.

These builder materials may be present at a level of, for example, from 5 to 80% by weight, preferably from 10 to 60% by weight.

Apart from the components already mentioned, the detergent compositions of the invention may contain any of the conventional additives in the amounts in which such materials are normally employed in fabric washing detergent compositions. Examples of these additives include lather boosters, such as alkanolamides, particularly the monoethanol amides derived from palmkernel fatty acids and coconut fatty acids, lather depressants, such as alkyl phosphates and silicones, anti-redeposition agents, such as sodium carboxymethyl cellulose and alkyl or substituted alkyl cellulose ethers, other stabilizers, such as ethylene diamine tetraacetic acid, fabric softening agents, inorganic salts, such as sodium sulphate, and, usually present in very small amounts, fluorescent agents, perfumes, enzymes, such as proteases, cellulases, lipases and amylases, germicides and colourants.

The bleaching compositions described herein are useful in a variety of cleaning products. These include laundry detergents, laundry bleaches, hard surface cleaners, toilet bowl cleaners, automatic dishwashing compositions and even denture cleaners. They may be used in a variety of product forms including powders, on sheets or other substrates, in pouches, in tablets or in non-aqueous liquids, such as liquid nonionic detergents. They may also be conveniently used in detergent composition wherein the peroxyacid bleach and the hydrogen peroxide source are preconcentrated within a sachet or are compressed into a tablet form.

Generally, for reasons of stability and handling, the bleach precursors will advantageously be presented in the form of particulate bodies comprising said bleach precursor and a binder or agglomerating agent. Many diverse methods of preparing such precursor particulates have been described in various patent literature documents, such as for example Canadian Patent No. 1,102,966; British Patent No. 1,561,333; U.S. Pat. No. 4,087,369; EP-A-0,240,057; EP-A-0,241,962; EP-A-0,101,634 and EP-A-0,062,523. Any of these methods may be selected and applied to the bleach compositions of the invention.

Particulates incorporating the peroxyacid bleach precursors are normally added to the spray-dried portion of the detergent composition with the other dry-mix ingredients, such as enzymes, inorganic peroxygen bleaches and suds depressants. It will be appreciated, however, that the detergent composition to which the precursor particulates are added may itself be made in a variety of other ways, such as dry-mixing, agglomeration, granulation, extrusion, compacting and densifying processes etc., such ways being well known to those skilled in the art and not forming part of the present invention.

The peroxyacid bleach precursors may also be incorporated in detergent additive products. Such additive products are intended to supplement or boost the performance of conventional detergent compositions and may contain any of the components of such compositions, although they will not comprise all of the components present in a fully formulated detergent composition. Additive products in accordance with this aspect of the invention will normally be added to an aqueous liquor containing a source of (alkaline) hydrogen peroxide, although in certain circumstances a source of alkaline hydrogen peroxide may be included in the product.

Additive products in accordance with this aspect of the invention may comprise the peroxyacid bleach precursor alone in combination with a carrier, such as a compatible particulate substrate, a flexible non-particulate substrate or a container (e.g. pouch or sachet).

Examples of compatible particulate substrates include inert materials, such as clays and other aluminosilicates including zeolites both natural and synthetic of origin. Other compatible particulate carrier materials include hydratable inorganic salts, such as phosphates, carbonates and sulphates.

Additive products enclosed in bags or containers can be manufactured such that the containers prevent egress of their contents when dry but are adapted to release their contents on immersion in an aqueous solution.

In a further specific embodiment, the peroxyacid bleach precursors are suitably incorporated in so-called non-aqueous liquid laundry detergent compositions together with a peroxide bleaching compound, e.g. sodium perborate, to impart an effective cleaning and stain-removing capacity to said products when used on fabrics and textiles.

Non-aqueous liquid detergent compositions including paste-like and gelatinous detergent compositions in which the peroxyacid bleach precursors may be incorporated are known from the art and various formulations have been proposed, e.g. in U.S. Pat. Nos. 2,864,770; 2,940,938; 4,772,412; 3,368,977; GB-A-1,205,711; 1,270,040; 1,292,352; 1,370,377; 2,194,536; DE-A-2,233,771; and EP-A-0,028,849.

These are compositions which normally comprise a non-aqueous liquid medium with or without a solid phase dispersed therein. The non-aqueous liquid medium may be a liquid surfactant, preferably a liquid nonionic surfactant; a non-polar liquid medium, e.g. liquid paraffin; a polar solvent, e.g. polyols, such as glycerol, sorbitol, ethylene glycol, optionally combined with low-molecular monohydric alcohols, e.g. ethanol or isopropanol; or mixtures thereof.

The solid phase be builders, alkalis, abrasives, polymers, clays, other solid ionic surfactants, bleaches, enzymes, fluorescent agents and other usual solid detergent ingredients.

The invention will now be illustrated by way of the following non-limiting examples:

EXAMPLES

The Synthesis of

[AcOCH$_2$CH(CHOAc)$_3$(CHOCOR)O]

i) 2,3,4,6-Tetraacetylglucose (TAG)

1,2,3,4,6-Pentaacetylglucose (39 g, 0.1 mol) was dissolved in ethylacetate (250 ml) at room temperature with stirring. To this solution was added dimethylsulphoxide (DMSO, 5 ml) and 2-aminoethanol (15.25 g, 0.25 mol) and the solution was stirred at room temperature for 5 hours. The reaction was monitored by t.l.c (alumina) eluted with ether until all starting material had disappeared. The resulting ethyl acetate solution was washed with water (2 times with 250 ml) and dried over anhydrous sodium sulphate. After filtration, the solvent was removed under reduced pressure to yield an oil (28.0 g), yield 80%.

$^1$H nmr ($\delta$ CDCl$_3$):- 2.02 (s, 3H, COCH$_3$), 2.03 (s, 3H, COCH$_3$), 2.1 (s, 3H, COCH$_3$), 2.11 (s, 3H, COCH$_3$), 3.08 (s, 1H, OH), 4.15 (m, 1H, HCCH$_2$+OCOCH$_3$), 4,25 (m, 1H, HCOCOMe), 4.28 (s, 1H, HCOCOMe), 4.9 (m, 1H, HCOCOMe), 5.1 (t, 2H, —CH$_2$OCOMe), 5.47 (m, 1H, HC(O-)OCOMe), 5.55 ppm (t, 1H, HCOCOMe).

ii) 1-Benzoyl-2,3,4,6-tetraacetylglucose (III) - BTAG 2,3,4,6-Tetraaacetylglucose (12 g, 0.034 mol) was placed in a flask equipped with a stirrer, condensor, and drying tube (calcium chloride). To this flask was added ethylacetate (100 ml) and triethylamine (3.5 g, 0,035 mol). The mixture was stirred to dissolve the tetraacetylglucose. Benzoic anhydride (8 g, 0.034 mol) was added to the mixture, which was then stirred at room temperature for 6 hours. This solution was washed with water (2 times 100 ml), dried over anhydrous sodium sulphate, filtered, and the solvent removed in vacuo to yield an off-white solid (15 g). This solid was recrystallised from ethanol to give needles (13g), yield 84%: mpt 122°–124° C.;

$^1$H nmr assay (DMSO, succinic acid) 97.3%, ($\delta$ CDCl$_3$):- 2.64 (s, 3H, COCH$_3$), 2.8 (s, 3H, COCH$_3$), 2.1 (s, 3H, COCH$_3$), 2.11 (s, 3H, COCH$_3$), 4.12 (dd, 1H, HCCO), 4.3 (dd, 1H, HCCO), 4.4 (m, 1H, HCCO), 5.14 (t, 1H, C$\underline{H}$—CH$_2$OAc), 5.24 (t, 2H, CH$_2$OAc), 5.65 (t, 1H, HC$\overline{CO}$), 6.3 (d, 1H, HC(OCOR)CO), 7.65 (t, 2H, ArH), 7.8 (t, 1H, ArH), 8.0 ppm (d, 2H, ArH); i.r. (nujol) $v$ 1735 cm−1.

iii) 1-Hexanoyl-2,3,4,6-tetraacetylglucose (II) - HTAG

This material was synthesised using a method analogous to that used in example (ii), except hexanoyl chloride was used instead of benzoic anhydride. The product was a yellow oil (16 g). This oil was crystallised in two portions from hot ethanol/water. White crystals were obtained (6.48 g) yield 41%.

$^1$H nmr assay (CDCl$_3$, trioxan), 95% ($\delta$ CDCl$_3$):- 0.9 (t, 3H, CH$_3$), 1.3 (m, 4H, CH$_2$CH$_2$CH$_3$), 1.6 (m, 2H, COCH$_2$CH$_2$), 2.02 (3s, 9H, COCH$_3$), 2.1 (s, 3H, COCH$_3$), 2.37 (t, 2H, COCH$_2$), 3.85 (m, 1H, HCOAc), 4.1 (dd, 1H, HCOAc), 4.3 (1H, dd, HCOAc), 5.15 (m, 2H, CH$_2$OAc), 5.25 (m, 1H, HCOAc ), 5.73 ppm (d, 1H, HC(OCOR)OAc); i.r. (nujol) $v$ 1740 cm−1.

iv) 1-Butanoyl-2,3,4,6-tetracetylglucose (I) - BUTAG

This material was prepared using a method analogous to that used in example (ii) except butanoyl chloride was used instead of benzoic anhydride. The product was a yellow oil (13.5 g) which was difficult to crystallise from ethanol/water. However, some white needles were obtained (1.6 g), yield 11%:

$^1$H nmr ($\delta$ CDCl$_3$):- 0.93 (t, 3H, CH$_3$), 1.65 (m, 2H, CH$_2$CH$_3$), 2.05 (3s, 9H, COCH$_3$), 2.1 (s, 3H, COCH$_3$), 2.35 (t, 2H, COCH$_2$), 3.85 (m, 2H, HCOAc), 4.1 (dd, 1H, HCOAc), 4.3 (dd, 1H, HCOAc), 5.15 (m, 2H, CH$_2$OAc), 5.25 (m, 1H, HCOAc), 5.73 ppm (d, 1H, HC(OCOR)O); i.r. (nujol) $v$ 1740 cm−1.

v)
1-(3'-Trimethylammoniumtoluoyl)-2,3,4,6-tetraacetyl-glucose (IV) - QTAG

This was prepared in two steps. The first step was analogous to the preparation used in example (ii), except 3-chloromethylbenzoyl chloride (0.03 mol) was used in replace of benzoic anhydride. The product was a yellow oil (13.92 g), yield 93%:

$^1$H nmr ($\delta$ CDCl$_3$):- 2.0 (s, 3H, COCH$_3$), 2.08 (3s, 9H, 3XCOCH$_3$), 3.95 (m, 1H, HCOAc) 4.15 (m, 1H, HCOAc), 4.32 (m, 1H, HCOAc), 4.62 (s, 2H, ArCH$_2$Cl, $\beta$-anomer), 4.68 (s, 2H, ArCH$_2$Cl, $\alpha$-anomer), 5.2 (m, 2H, HCOAc), 5.35 (dd, 1H, HCOAc), 5.93 {d, 1H, H(COR)O, $\alpha$-anomer (75%)}, 6.6 {d, 1H, HC(COR)O, $\alpha$-anomer (25%)}, 7.5 (m, 1H, ArH), 7.65 (m, 1H, ArH), 8.0 ppm (m, 2H, ArH). The second step involved dissolving 3'-chloromethylbenzoyl-2,3,4,6-tetraacetyl-glucose (13 g, 0.025 mol) in sodium-dried ether (250 ml), and adding trimethylamine (7 ml, 33% solution in dimethoxyethane). The mixture was left standing for 72 hours. A white precipitate formed which was removed by filtration and washed with ether. This white solid was dried in vacuo (4.04 g, 28% yield):- $^1$H nmr Assay (D$_2$O/trioxan) 91% ($\delta$ D$_2$O):- 2.0 (s 3H COCH$_3$), 2.07 (s,3H, COCH$_3$), 2.14 (s, 6H, 2×COCH$_3$), 3.13 (s, 9H, +NMe$_3$), 4.2 (m, 1H, HCOAc), 4.32 (m, 2H, HCOAc, 4.6 (s, 2H, ArCH$_2$N+), 5.3 (m, 2H, CH$_2$OAc), 5.6 (t, 1H, HCOAc), (6.18(d, 1H, H(COR) $\beta$-anomer 75%), 6.6 (d, 1H, H(COR) $\alpha$-anomer 25%)}, 7.6 (m, 1H, ArH) , 7.9 (m,1H, ArH), 8.2 (m, 2H, ArH).

(vi)
1-(6'-Trimethylammoniumhexanoyl)-2,3,4,6-tetraacetyl-glucose bromide (V) - QHTAG This material was prepared in two steps. The first step was analogous to the preparation used in example (ii) using 6-bromohexanoyl chloride (0.08 mol) instead of benzoic anhydride. The product was crystallised from ethanol/water to give plate-like crystals (25.3 g; 60% yield).

$^1$H nmr ($\delta$ CDCl$_3$) 1.5 (m, 2H,CH$_2$CH$_2$CH$_2$Br), 1.65 (m, 2H, CH$_2$CH$_2$Br), 1.85 (p, 2H, CH$_2$CH$_2$CO), 2.02 (s, 3H,COCH$_3$), 2.04 (s, 6H, 2×COCH$_3$), 2.1 (s, 3H, COCH$_3$), 2.4 (m, 2H, CH$_2$CO), 3.4 (t, 2H, CH$_2$Br), 3.85 (m, 1H, HCOAc), 4.1 (dd, 1H, HCOAc), 4.3 (dd, 1 H, HCOAc), 5.1 (m, 2H, CH$_2$OAc), 5.25 (t, 1H, HCOAc), 5.71 (d, 1H, HC(COR)O).

The second step involved dissolving 1-(6'-bromohexanoyl)-2,3,4,6-tetraacetylglucose (8g, 0.015 mol) in dry dimethoxyethane (50 ml), and adding trimethylamine (1.6g, 1.7 XS). The mixtures was stirred at room temperature for 48 hours. An insoluble white solid was formed, which was removed by filtration and washed with ether (50ml). The solid was dried in vacuo, (7.0 g; 79% yield). 1H nmr Assay (DMSO/trioxan) 94%. 1H nmr ($\delta$ D$_2$O) 1.4 (p, 2H, CH$_2$CH$_2$CH$_2$CO), 1.68 (p, 2H, CH$_2$CH$_2$CO), 1.84 (p, 2H, CH$_2$CH$_2$N+), 2.08 (s, 3H, COCH$_3$), 2.12 (s, 6H, 2×COCH$_3$), 2.15 (s, 3H, COCH$_3$), 2.5 (t, 2H, CH$_2$CO), 3.14 (s, 9H, +NMe$_3$). 3.3 (m, 2H, CH$_2$N+), 4.2 (d, 1H, HCOAc), 4.4 (dd, 1H, HCOAc), 5.2 (dd, 2H, CH$_2$OAc), 5.45 (t, 1H, HCOAc), 5.95 (d, 1H, HC(OCOR)O).

vii) 1-(4'-Trimethylammoniumbutanoyl)-2,3,4,6-tetraacetyl-glucose bromide - QBTAG This material was prepared in two steps. The first step was analogous to the preparation of used in example vi), using 4-bromobutanoyl chloride (0.04 mol) instead of 6-bromohexanoyl chloride. The product was crystallised from ethanol/water to give plate-like crystals (9.83 g; 50% yield).

$^1$H nmr ($\delta$ CDCl$_3$):- 2.01 (s, 3H, COCH$_3$), 2.03 (s, 3H, COCH$_3$), 2.04 (s, 3H, COCH$_3$), 2.1 (s, 3H, COCH$_3$), 2.2 (m, 2H, CH$_2$CH$_2$Br), 2.6 (t, 2H, CH$_2$CO), 3.45 (t, 2H, CH$_2$Br), 3.85 (m, 1H, HCOAc), 4.1 (dd, 1H, HCOAc), 4.3 (dd, 1H, HCOAc), 5.15 (m, 2H, CH$_2$OAc), 5.25 (t, 1H, HCOAc), 5.72 (d, 1H, HC(OCOR)O). The second step was also analogous to the preparation of (V), except that 1-(4'-bromobutanoyl)-2,3,4,6-tetraacetyl-glucose (0.0161 mol) was used instead of 1-(6'-bromohexanoyl)-2,3,4,6-tetraacetylglucose. The product was dried in vacuo, (7.35 g; 82% yield) mpt 170°–171° C.

$^1$H nmr Assay (CDCl$_3$/pyrazine) 94%. $^1$H nmr ($\delta$ CDCl$_3$), 2.02 (s, 3H, COCH$_3$), 2.04 (s, 3H, COCH$_3$), 2.08 (s, 3H, COCH$_3$), 2.12 (s, 3H, COCH$_3$), 2.15 (m, 2H, CH$_2$CH$_2$CO), 2.63 (t, 2H, CH$_2$CO), 3.48 (s, 9H, +NMe$_3$), 3.78 (m, 2H, CH$_2$N+), 3.85 (m, 1H, HCOAc), 4.13 (dd., 1H, HCOAc), 4.3 (dd, 1H, HCOAc), 5.12 (m, 2H, CH$_2$OAc), 5.25 (t, 1H, HCOAc), 5.68 (d, 1H, HC(COR)O).

viii) 1,octyl,2,2′,3,3′,4,6,6′-hepta-acetyl lactose (OHAL)

Lactose (34.2 g 0.1 mol) was added to a large flask equipped with a reflux condenser and acetic acid (200 ml) was added with sodium acetate (4 g). This mixture was heated to 120° C. and acetic anhydride (102 g 1 mol ;XS) was added dropwise with stirring over a period of 1 hour. After the addition was complete the mixture was maintained at this temperature, with stirring, for a further 8 hours. Then the mixture was cooled to room temperature and the pH adjusted to 7 by addition of sodium hydroxide solution (aqueous 2M). The resulting mixture was transferred to a separating funnel and extracted with water (500 ml) and ethyl acetate (2×500 ml). The ethyl acetate was combined and washed with sodium bicarbonate solution (200 ml), water (200 ml) and brine (500 ml). The ethyl acetate solution was dried over anhydrous sodium sulphate, filtered and concentrated under reduced pressure to give a white 'sticky' solid which was dried under vacuo to give a white powder (61.2 g; yield 92%). [Lactose octaacetate]. This material was recrystallised from ethanol to give fine plates (30 g) ($v$ nujol) 1750 cm$^{-1}$ ($\delta$ CDCl$_3$) 5.65 ((d) 1H OCH-OAc); 5.37 ((d) 1H CH-OAc); 5.23 ((t) 1H CH-OAc); 5.1 (m 2H 2×CH-OAc); 4.95 ((dd) 1H CH-OAc); 4.46 ((dd) 2H CH$_2$OAc); 4.1 (m 3H CH$_2$-OAc+CHOAC); 3.87 (2H 2×CH-O); 3.75 (m 1H CHOAc); 2.18 (s 3H COCH$_3$); 2.12 (s 3H COCH$_3$); 2.1 (s 3H COCH$_3$); 2.06 (s 3H COCH$_3$); 2.05 (s 3H COCH$_3$); 2.03 (s 3H COCH$_3$); 2.02 (s 3H COCH$_3$); 1.95 (s 3H COCH$_3$).

Lactose octa acetate (29 g 0.044 mol) was dissolved in ethyl acetate (400 ml) containing dimethyl sulphoxide (4 g) and ethanolamine (6.7 g 0.11 m; 2.5×excess). The resulting mixture was stirred at room temperature and analysed periodically by thin layer chromatography (TLC). The reaction was monitored in this way until all of the octa acetate was removed, ca 2 hours. The ethyl acetate was extracted with water (3×200 ml), brine (200 ml) and dried over sodium sulphate. The solution was filtered and concentrated to dryness under vacuo to yield a white solid which was dried in vacuo to give a white powder (25.2 g; yield 91%). [2,2′,3,3′,4′,6,6′ heptaacetyl lactose] ($v$ nujol 3500; 1750 cm$^{-1}$.

Lactose heptaacetate (6 g 0.1 mol) was dissolved in ethyl acetate (100 mls) containing triethylamine (7.3 g XS) and to this stirred solution was added octanoyl chloride (1.9 g 0.011 mol) in ethyl acetate (20 ml) over a period of 10 mins. A white precipitate formed during the reaction which was left stirring for a further 6 hours. After this period, water (100 ml) was added and the mixture separated. The ethyl acetate was washed with water (100 ml), brine (100 ml) and dried over sodium sulphate. The resulting solution was filtered and concentrated under vacuo and the resulting solid dried in vacuo. The product was a yellow/white 'sticky' solid. (5 g; yield 70%) (OHAL) $^1$Hnmr Assay (CDCl$_3$; Trioxan 96%) ($\delta$ CDCl$_3$) 6.2 ((d) $^1$H$^1$ CHOCOR $\beta$ anomer); 5.7 (d '1H' CHOCOR $\alpha$ anomer); 5.43 (t 1H CH OAc); 5.35 (d 1H CHOAc); 5.1 (m 1H CHOAC); 4.1 (m 3H CH$_2$OAc+CHOAc); 3.85 (m 3H 3×CHOAc); 2.42 (t '2H ' CH$_2$COO $\beta$ anomer); 2.12 (t '2H ' CH$_2$COO $\alpha$ anomer); 2.16 (s 3H COCH$_3$); 1.95 (s 3H COCH$_3$); 1.7 (m 3H CH$_2$CH$_2$COC)); 1.3 (m 8H—(CH$_2$)$_4$—); 0.9 (m 3H —CH$_3$). ($v$ nujol) 1750 cm$^{-1}$.

EXAMPLE ix

Bleaching experiments were carried out in a stirred, thermostatted vessel, kept at constant pH using a Radiometer Titralab. The pH was adjusted using 0.1M NaOH. Precursor was added to 100 ml distilled, deionised water containing 2×10$^{-5}$M of the stabilizer ethylenediaminetetra(methylene phosphonic acid)—Dequest ~2040 -, two discs of standard tea-stained test cloths (liquor to cloth ratio =100:1), and H$_2$O$_2$ (10-2M, 160 ppm Avox). The precursor was added directly or as an acetone solution, such that the precursor concentration was 10$^{-3}$M, or 5×10$^{-4}$M for precursors capable of delivering two or more equivalents of peroxyacid. Bleaching performance was determined by using a Instrumental Colour Systems Micro-match to measure the change in reflectance at 460 nm, and is reported as $\Delta$R460*. At pH 10 and 40° C., residual bleaching by hydrogen peroxide alone was 1.70 units.

| Precursors | [P]/M × 10$^{-4}$ | pH | Temp. °C. | $\Delta$R460* tea |
|---|---|---|---|---|
| — | 0.00 | 10 | 40 | 1.7 |
| TAED | 4.84 | 10 | 40 | 3.4 |
| PAG* | 5.02 | 10 | 40 | 3.4 |
| BTAG* | 4.68 | 10 | 40 | 5.9 |
| BuTAG* | 5.01 | 10 | 40 | 4.1 |
| QTAG | 12.50 | 10 | 40 | 18.3 |
| QETAG** | 4.88 | 10 | 40 | 7.3 |
| QBTAG** | 5.28 | 10 | 40 | 14.6 |

*Precursor dissolved in 1 ml acetone before use.
**QETAG = 1 - (2′-trimethylammonium acetyl) - 2,3,4,6 - tetraacetyl glucose
QBTAG = 1 - (4′-trimethylammonium butanoyl) - 2,3,4,6 - tetraacetyl glucose Data for TAED and PAG are included for comparison. The results show improved bleach performance on tea stains of the bleach precursor of the invention compared to TAED and PAG.

EXAMPLE x

Bleaching experiments were carried out in a stirred thermostatted vessel, kept at constant pH.

98 ml deionised water, 1 ml Dequest 2041 (2×10$^{-3}$M) were added to a vessel and the pH adjusted to pH 8.5, using 0.1M NaOH. In rapid succession H$_2$O$_2$, 1 ml of precursor (5×10$^{-2}$M) and two stained* test cloths were added.

* The stains were prepared as follows:- A gravy/oil mixture (10 g cooking oil, 10 teaspoons gravy granules, 600 ml water) was prepared and applied to desized test cloths. The stained test cloths were aged for two weeks before use.

The test cloths were left in the solution for 30 minutes. Throughout the experiment the temperature was maintained at 40° C.

Bleaching performance was determined as described in example ix.

In one set of experiments 0.2 ml of H$_2$O$_2$ (5×10$^{-2}$M) was used. In the other set of experiments 2.0 ml H$_2$O$_2$ (0.5M) was used.

The results obtained were as follows:

| | Precursor | | |
|---|---|---|---|
| H$_2$O$_2$: precursor ratio | BTAG | OTAG** | OHAL |
| 2.1 | 2.7 | 0 | 0.6 |

-continued

| H₂O₂: precursor ratio | Precursor | | |
|---|---|---|---|
| | BTAG | OTAG** | OHAL |
| 20:1 | 3.1 | 0 | — |

The values given are $\Delta\Delta R_{460}$ with respect to OTAG.
**OTAG - 1-Octanoyl-2,3,4,6-tetraacetylglucose. Prepared using a method analogous to that used in example (ii) except octanoyl chloride (0.027 mol) was used instead of benzoic anhydride.

The results show BTAG and OHAL are more effective than OTAG on oily stains at low DH. This is advantageous as there is a trend in detergent formulations to lower pH conditions. This advantage is maintained at low precursor: hydrogen peroxide ratios, advantageous for economical reasons.

We claim:
1. A bleaching composition comprising:
  (a) from 0.1 to 20% by weight of a peroxyacid bleach precursor having a formula selected from the group consisting of:

$$R^I\text{—CH(CHOAc)}_n(CR^{II}OCOR)O; \quad (I)$$

and $$OCH(CH_2OAc)(CHOAc)_3CH— \quad (II)$$

$$—O—CH(CHOAc)_2(CHOCOR^{IV})OCH(CH_2OAc)$$

wherein:
Ac is $$\overset{O}{\underset{\|}{CH_3C}}—;$$

$R^I$ and $R^{II}$ may each independently be AcOCH₂ or H; and

R is a quaternary ammonium substituted derivative of a radical selected from the group consisting of
  (i) linear or branched chain C₃–C₆ alkyl, alkenyl or alkynyl groups,
  (ii) phenyl and substituted phenyl,
  (iii) C₁–C₄ alkyl phenyl, CH₂OCOR$^{III}$ and CH₂NHCOR$^{III}$ wherein R$^{III}$ is R; and n is 2 or 3; and R$^{IV}$ is a quaternary ammonium substituted derivative of a radical selected from the group consisting of
  (iv) linear or branched chain C₃₋₁₉ alkyl, alkenyl or alkynyl groups;
  (v) phenyl and substituted phenyl;
  (vi) C₁₋₄ alkyl phenyl, CH₂OCOR$^V$ and CH₂NHCOR$^V$ wherein R$^V$ is R$^{IV}$; and
(b) from 2 to 40% by weight of a source of hydrogen peroxide.

2. A composition according to claim 1 wherein in the compound of formula II the R$^{IV}$ is a C₇ alkyl group.

3. A composition according to claim 1 wherein the peroxyacid bleach precursor is 1-(3'-trimethylammoniumtoluoyl)-2,3,4,6-tetraacetylglucose.

4. A composition according to claim 1 wherein the peroxyacid bleach precursor is 1-(6'-trimethylammoniumhexanoyl)-2,3,4,6-tetraacetylglucose bromide.

5. A composition according to claim 1 wherein the peroxyacid bleach precursor is 1-(2'-trimethylammonium acetyl)-2,3,4,6-tetraacetylglucose and 1-(4'-trimethylammonium butanoyl)-2,3,4,6-tetraacetyl glucose.

6. A composition according to claim 1 wherein the molar ratio of the hydrogen peroxide source to the peroxyacid bleach precursor is from 0.5:1 to 20:1.

7. A composition according to claim 1 further comprising a surface-active material selected from the group consisting of a soap, anionic, nonionic, amphoteric, zwitterionic and cationic material and mixtures thereof; and a detergency builder.

* * * * *